(12) United States Patent
Sawada et al.

(10) Patent No.: US 6,184,517 B1
(45) Date of Patent: *Feb. 6, 2001

(54) PARTICLE ANALYZER SYSTEM

(75) Inventors: Tsuguo Sawada; Takehiko Kitamori; Toshitsugu Ueda; Seiichi Naitou; Hisao Takahara; Yukihiko Takamatsu, all of Tokyo (JP)

(73) Assignee: Yokogawa Electric Corporation, Tokyo (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/061,848

(22) Filed: Apr. 18, 1998

(30) Foreign Application Priority Data

Apr. 22, 1997 (JP) .................................................. 9-103770

(51) Int. Cl.[7] ........................................................ G01V 8/00
(52) U.S. Cl. ........................... 250/222.2; 250/458.1; 356/73; 356/335
(58) Field of Search ............................... 250/222.2, 458.1; 356/73, 335, 336, 337, 338, 342, 343

(56) References Cited

U.S. PATENT DOCUMENTS

| 4,710,025 | * | 12/1987 | Wyatt et al. | 356/343 |
|---|---|---|---|---|
| 4,957,363 | * | 9/1990 | Takeda et al. | 356/73 |
| 4,986,657 | * | 1/1991 | Ohe | 356/73 |
| 5,106,187 | * | 4/1992 | Bezanson | 356/73 |
| 5,194,913 | * | 3/1993 | Myrick et al. | 356/301 |
| 5,443,793 | * | 8/1995 | Ehrlich et al. | 422/83 |
| 5,491,344 | * | 2/1996 | Kenny et al. | 250/461.1 |
| 5,825,485 | * | 10/1998 | Cohn et al. | 356/316 |
| 5,862,273 | * | 1/1999 | Pelletier | 385/12 |

* cited by examiner

Primary Examiner—Que T. Le
Assistant Examiner—Thanh X. Luu
(74) Attorney, Agent, or Firm—Monnray Kojima

(57) ABSTRACT

A particle analyzer system that reduces size and cost, wherein particles are introduced into a cell, then the particles are irradiate in the cell with a laser beam, then atomic emission of the particles generated by the irradiation of the laser beam is transmitted, then a spectrum is obtained of the photo emission so transmitted, and the spectrum of the photo emission is detected and the wavelength of the laser beam is, other than the wavelength of the emission of the particles, is used to provide a filter to block the intrusion of the wavelength of the laser beam in a stage proceeding the photo emission.

15 Claims, 7 Drawing Sheets

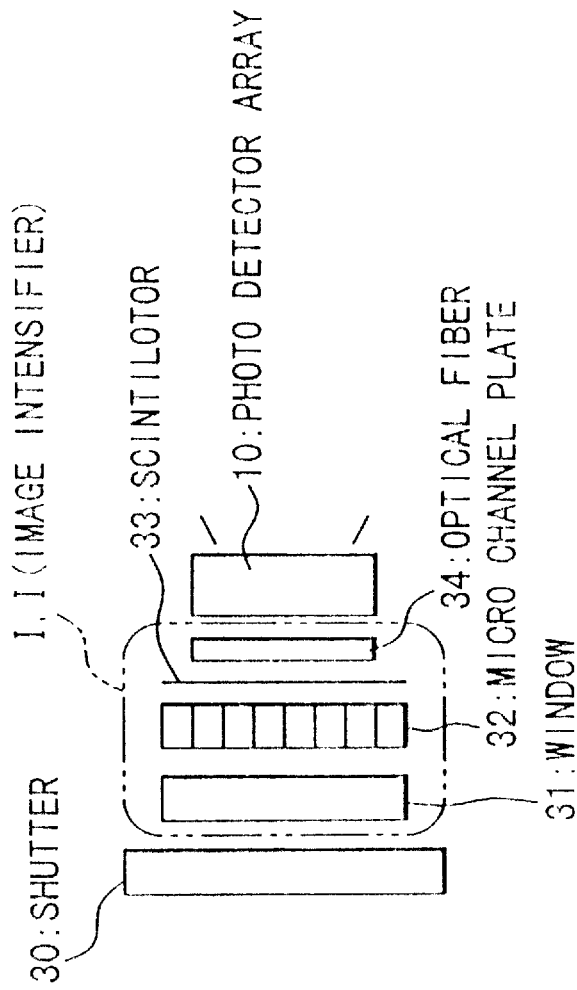
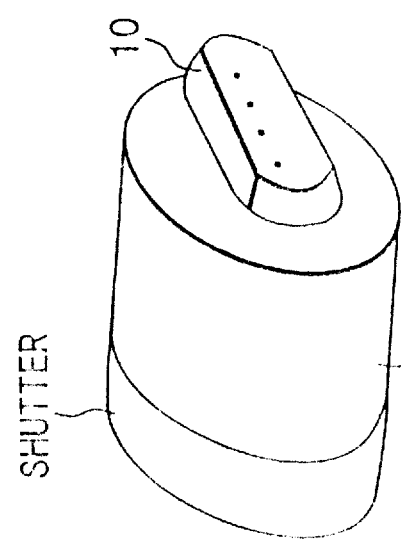

PARTICLE ANALYZER SYSTEM

BACKGROUND OF THE INVENTION

1 Field of Invention

This invention relates to a particle analyzer system that analyzes elements of fine particles, for example, suspended in a clean room or contained in purified water; and more particularly, to such a system which is of reduced size and cost.

2 Description of the Prior Art

FIG. 1 shows a conventional particle component analyzer system using a microwave induced plasma, and comprising a dispersion chamber 51 in which a filter 52 is provided. Solid particles (not shown) to be measured adhere to filter 52. An aspirator 53 draws in solid particles which are stuck on filter 52 and supplies them to discharge tube 54. In dispersion chamber 51, after the air is discharged with a suction pump (not shown), helium gas is introduced and maintained at a pressure which is slightly higher than atmospheric pressure. A microwave source 55 introduces microwaves into a cavity 56.

A detection window 57 is provided at the other end of the discharge tube 54 and four optical fibers 58 introduce the beam emitted from the detection window 57 into a plurality of spectometers (four Czerny-Turner monochromators in FIG. 1) 59. The outputs of the spectrometers 59 are applied to signal processor (CPU) 60.

When the microwaves of frequency 2.45 GHz are introduced into cavity 56 from source 55, plasma at a temperature of approximately 4000 K is generated in discharge tube 54. Solid particles, which are introduced into discharge tube 54 from the dispersion chamber 51 are atomized and ionized in the plasma. The particles emit light when they fall to the ground state after further excitation. This emission spectrum is taken out from the discharge tube 54 in the axial direction and are then subjected to spectrometric analysis by spectrometers 59. Then, the output signals from the spectrometers 59 are processed by the CPU 60 to measure and display the elements contained in the samples being measured.

In addition, a photoelectric converter (not shown) is provided for each spectrometer 59 to output electrical signals corresponding to the intensity of the light beams of selected wavelengths. Amplifiers (not shown) may be provided to amplify the output signals of the photoelectric converters. The amplifiers may be provided in the latter stages of each photoelectric converter. The sizes of the particles are, for example, classified into three types, by size, such as large, medium and small, corresponding to the values of the output signals from the amplifiers. The filter 52 has a predetermined area and aspirator 53 scans the filter 52 a plurality of times to draw in the same quantity of particles with each scan.

FIG. 2 shows the relationship between the emission wavelengths of the elements and the emission intensities and in practice about 50 elements are the object of the measurement. As seen in FIG. 2, for example, manganese (Mn) has an emission wavelength near 2600 Angstrom, and Aluminum (Al), fluorine (F), and oxygen (O) have emission wavelengths near 3950, 6900, and 7800 Angstrom, respectively.

Since photo emission is introduced into a plurality of spectrometers (e.g. four spectrometers) whose measuring wavelengths are fixed, only four components can be captured in one emission. Because the particles may contain a number of various elements, such as described above, the measurement may have to be carried out a plurality of times with the wavelength settings of the spectrometers being changed for each measurement. Thus, measurement with prior art devices takes a long time. Although the problem may be solved with use of a larger number of spectrometers to shorten the measuring time, this requires a very large system, and also increases the cost of such system,since spectrometers are expensive.

SUMMARY OF THE INVENTION

Accordingly, an object of the invention is to overcome and resolve the aforementioned deficiencies, disadvantages and problems of the prior art.

Another object is to provide a particle analyzer system wherein the measuring time is shortened and the system is made smaller and the cost thereof is lowered.

BRIEF DESCRIPTION OF THE DRAWINGS

FIGS. 7(A) and 7(B) are diagrams depicting an optical amplifying device.

DETAILED DESCRIPTION OF THE PREFERRED EMBODIMENTS

Figure 2:
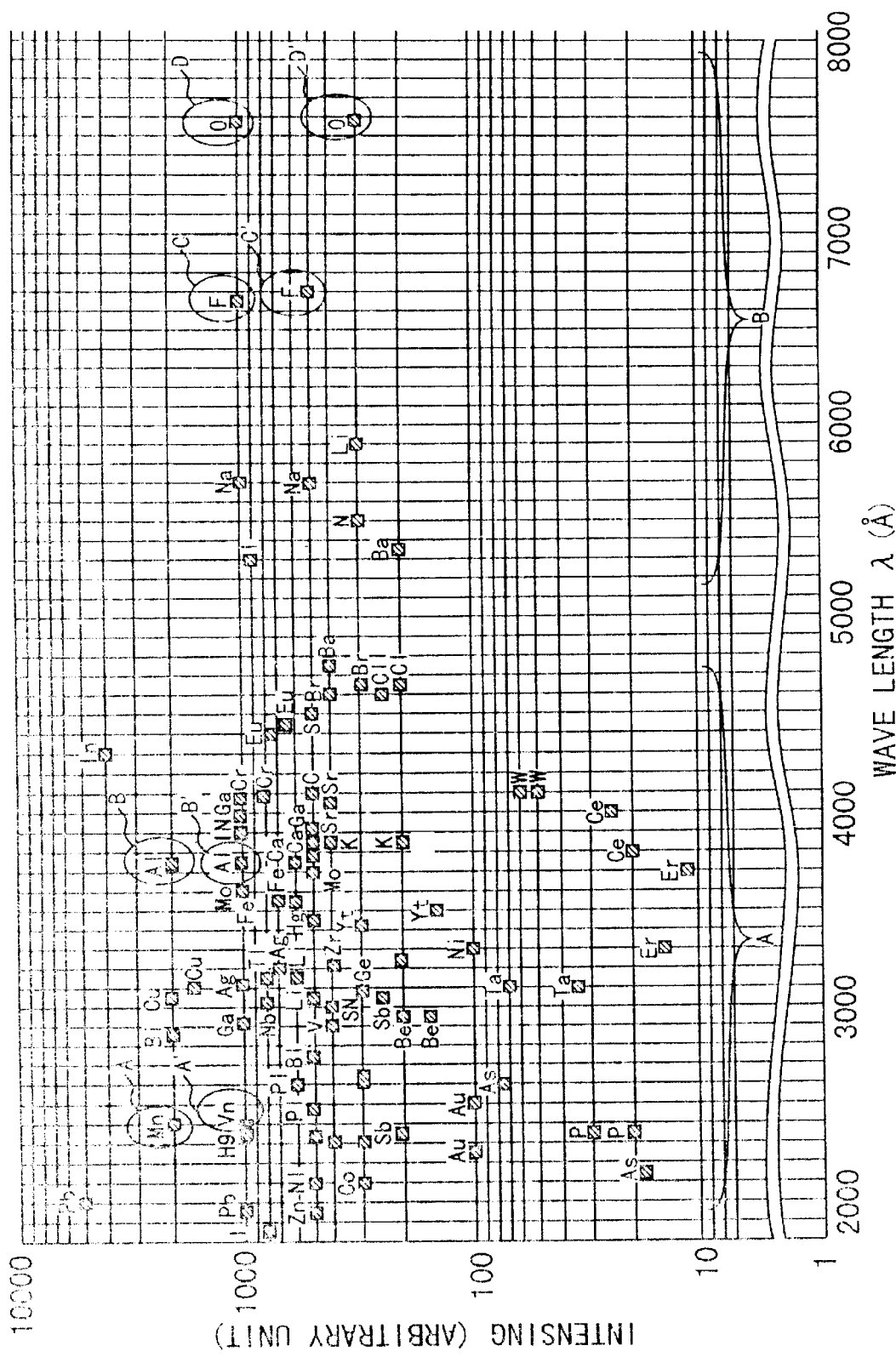
FIG. 2 is a graph depicting the relationship between the emission intensity of each element and the wavelength thereof.
Figure 3:
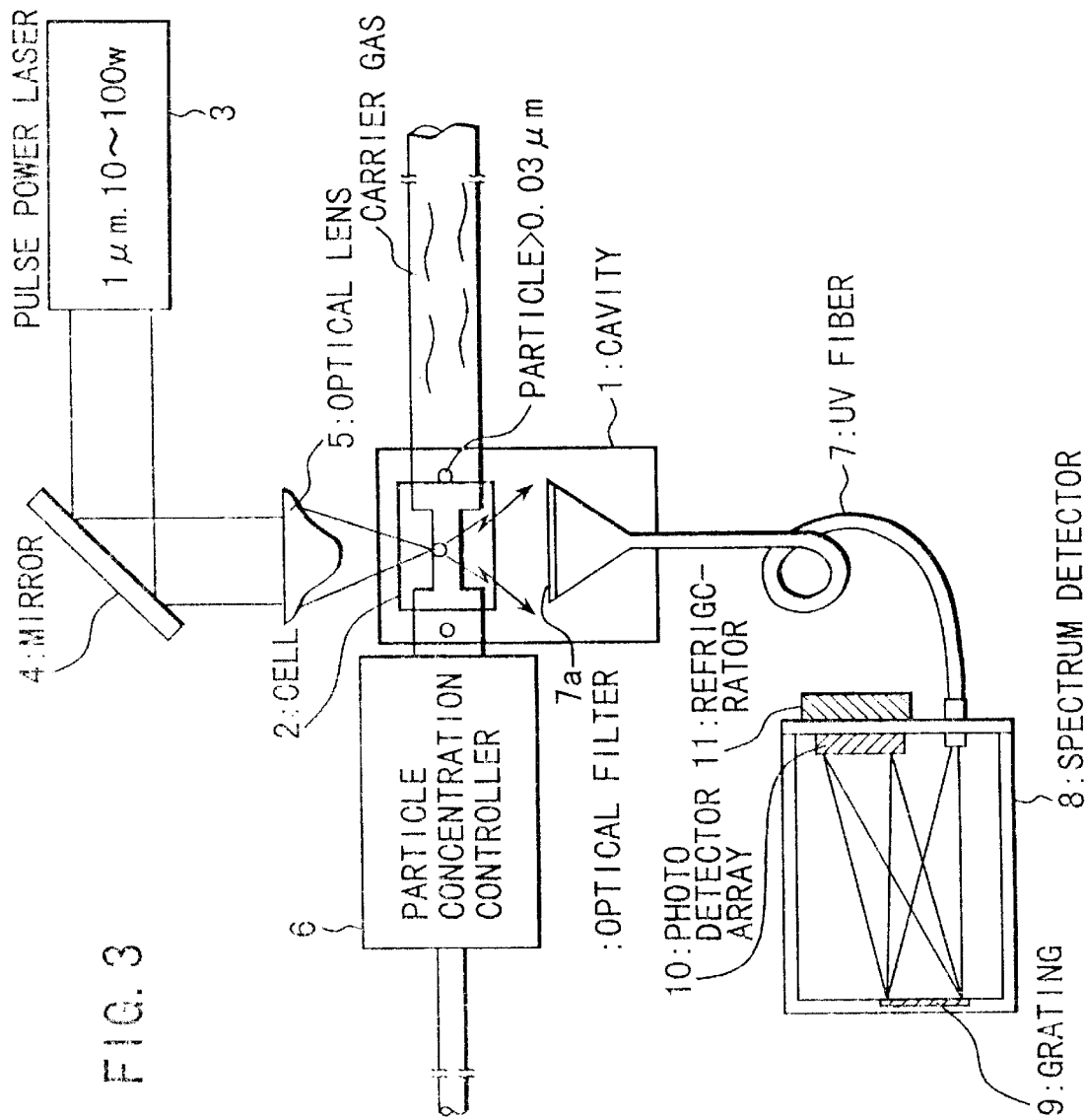
FIG. 3 is a diagram depicting major components of an illustrative embodiment of the invention.

FIG. 3 shows major components of a particle analyzer system of the invention comprising a cavity 1 in which external light is applied and vacuum ultraviolet emission is propagated without attenuation. Cell 2, consisting of a transparent material, is provided in cavity 1. A laser 3, which may be, for example, a yttrium aluminum garnet (YAG) laser whose output wavelength is approximtely 1 $\mu$m, intensity is 10 to 400 mJ/pulse, and pulse width is 10 to 100 ns, is used as a light source. It is preferable to use a wavelength of the laser beam outside the range of the wavelength of the photo emission from the elements, as measuring objects, so that the former is not superimposed on the latter, that is in the range of 0.15 to 0.9 $\mu$m.(see FIG. 2).

The generated laser beam is formed to have a diameter of about 0.1 mm via mirror 4 and optical lens 5 to irradiate the particles moving through the restriction of cell 2. A particle concentration controller 6 supplies the particles into cell 2. The controller 6 may comprise, for example, cyclones connected in multiple stages, as shown in FIG. 4.

Figure 4:
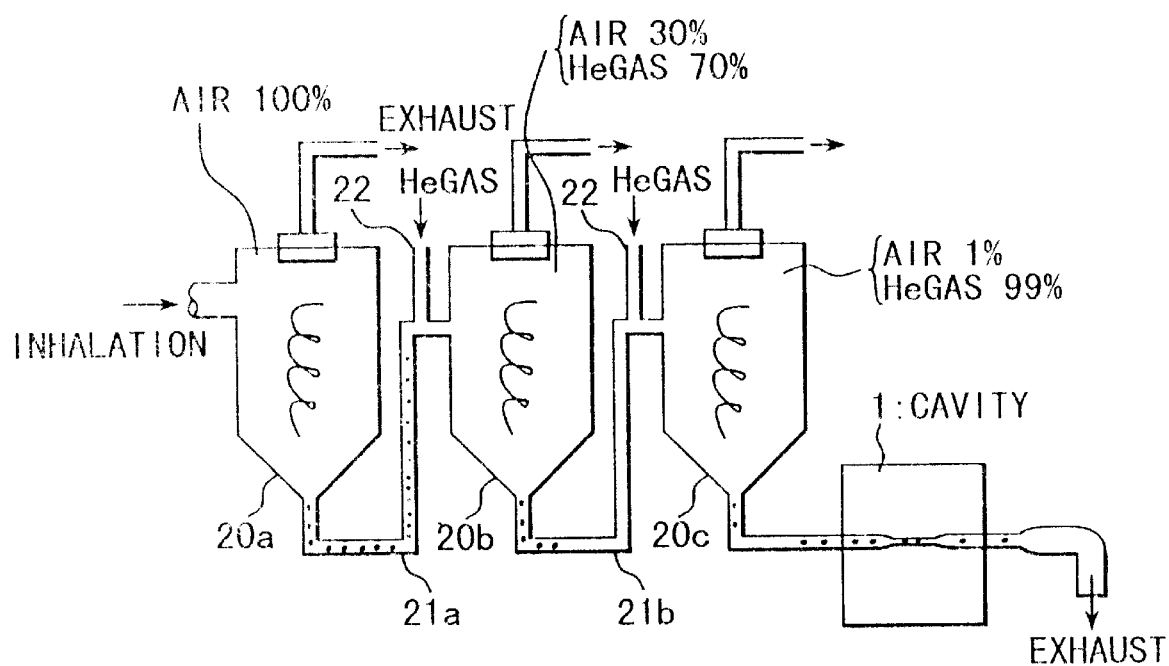
FIG. 4 is a cross-sectional view depicting a concentration control device for particles and a medium substitution mechanism.

In FIG. 4, the air in a clean room,for example, may contain slight traces of particles, and is drawn in from the inhalation of the first stage cyclone 20a. The air drawn in by cyclone 20a moves downward in a circular motion in the cyclone, as shown in FIG. 4, and then is drawn upward to the top of the cyclone. The particles contained in the air drawn into cyclone 20a are pressed against the inner wall of the cyclone by centrifugal forces and then are caused to fall to the mirror machined bottom of cyclone 20a The particles which have fallen are then caused to flow into the second cyclone 20b through tube 21a.

At the midpoint of tube 21a, an inert gas (such as helium (He) gas or argon (Ar) gas) is supplied to inlet 22. The particles are carried to the next stage cyclone 20b together with the inert gas, wherein He gas is substituted for the major part (e.g. 70%) of the medium (e.g. air) which carries the particles. The particles are then caused to drop toward the bottom of cyclone 20b and are carried through tube 21b to the next stage cyclone 20c.

Gas inlet 22 is also provided at the midpoint of tube 21b connecting cyclones 20b and 20c. Helium gas supplied through inlet 22 is further substituted for the medium (e.g. air) carrying the partical and, for example, the ratio of air to helium then becomes 1:99. In that manner, substitution of medium, while the particles are being carried, is implemented by using a plurality of stages of the cyclone In addition, the concentration of particles contained in the medium can be adjusted by adjusting the quantity of air drawn in at the first stage.

Figure 5:
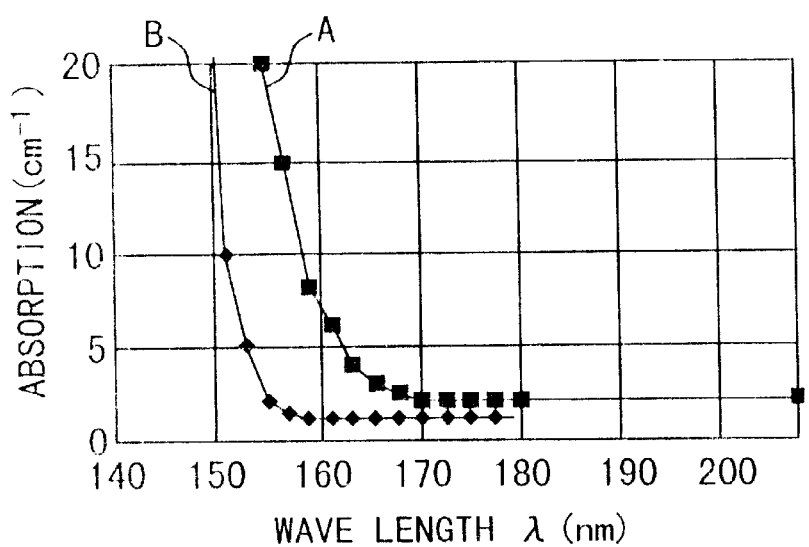
FIG. 5 is a graph depicting the relationship between the emission wavelength and the emission intensity for the optical fibers used in the invention.

Returning to FIG. 3, a length of bundled optical fibers 7 has one end thereof located in vacuum cavity 1 and the other end thereof connected to spectrum detector 8. A filter 7a blocks the intrusion of a laser beam and transmits photo emission wavelengths only from the particles. The optical fibers used herein will be described with reference to FIG. 5 which shows the relationship between the wavelength of the beam transmitted through the otpical fiber and the absorption coefficient. Curve A indicates the absorption characteristics of a commercially available quartz optical fiber and has relatively good characteristics. However, it is difficult to transmit a beam even with such a good optical fiber for the elements that generate photo emission at a wavelength equal to or below 1.6 $\mu$m. It is thus difficult to identify a specific component element. Absorption of the photo emission having short wavelengths by an optical fiber can be prevented by increasing the purity of the glass and by terminating dangling bonds between silicon and oxygen atoms with use of fluorine. In the invention, an optical fiber having the characteristic shown by curve B in FIG. 5 which is obtained by implementing the above discussed countermeasures, is used. Such an optical fiber can transmit the photo emission whose wavelength reaches vacuum ultra violet. At the tips of the optical fibers located in the vacuum cavity 1, a condenser lens is formed for each fiber and the end of the fiber takes the shape of a funnel as a whole, to gather the photo emission over a wide range.

Figure 6:
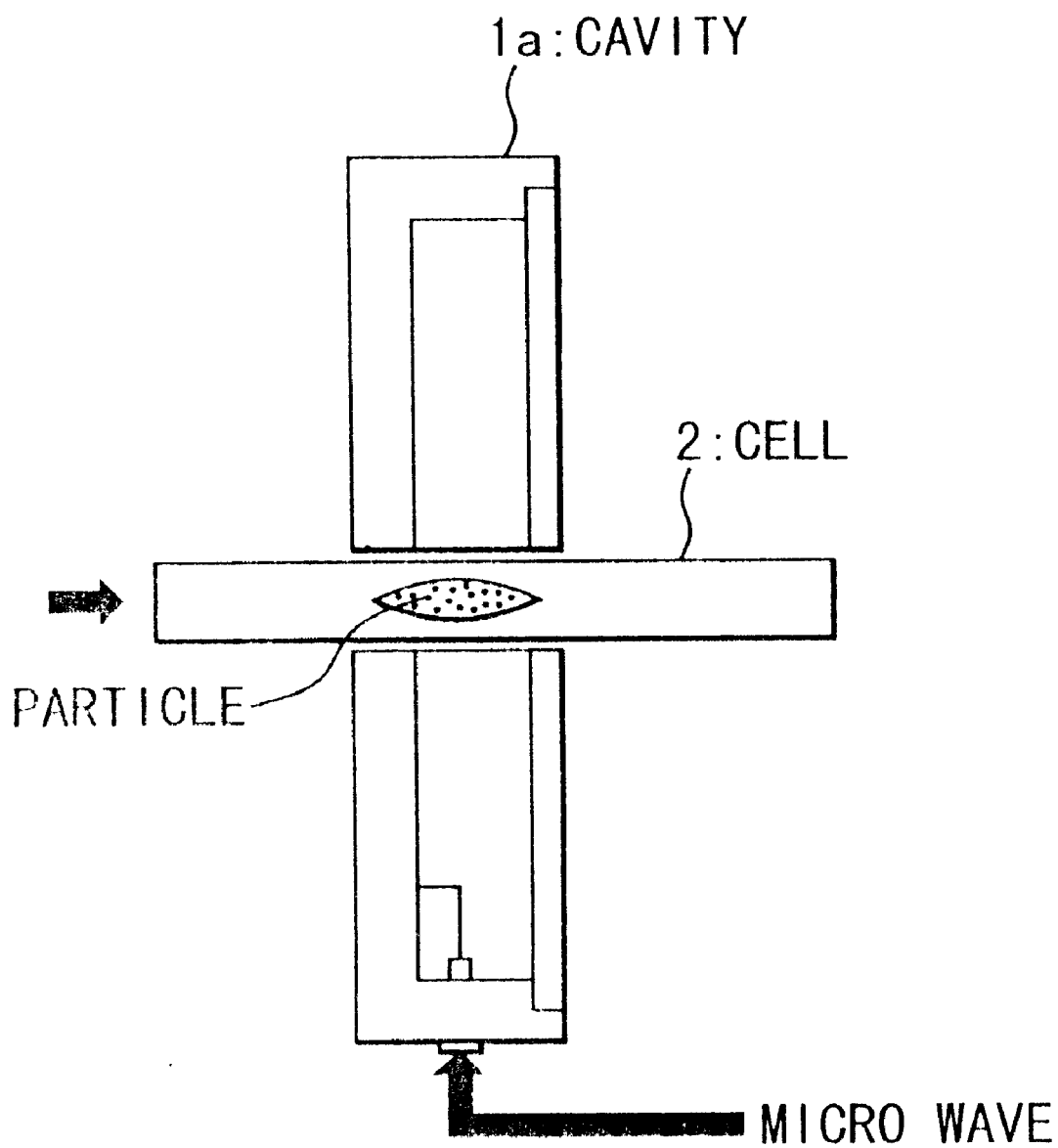
FIG. 6 is a cross-sectional view depicting a device for applying an electric field to the particles.

FIG. 6 shows an example of a device for applying an alternating electric field, such as microwaves, to the particles. A helium or argon gas, containing particles, flows through cell 2. A cavity into which microwaves, for example, of 2.5 GHz, are injected, forms a cavity resonator for the microwaves and has a hole through which cell 2 runs at the center thereof. Resonance occurs in the cavity 1a by injecting microwaves and energy is concentrated in the center portion.

Since beakdown of the particles is accelerated by application of the alternating electric field, the output power of a laser can be decreased.

Returning to FIG. 3, the photo emission concentrated by the optical fiber 7 is introduced into spectrum detector 8 evacuated to form a vacuum. Grating 9 receives the photo emission outputted from the optical fiber 7 and produces spectral lines. The spectral lines obtained by grating 9 are incident to the photo detector array 10, which may be, for example, a photo diode array. Photo detector array 10 is cooled with a refrigerator 11, which may use, for example Peltier elements or liquid nitrogen. Refrigerator 11 functions so that dark current of the photo detector is minimized and the noise level is lowered.

FIGS. 7(A) and 7(B) show a commercially available image intensifier (hereinafter called 'I.I.'), wherein FIG. 7(A) is a perspective view and FIG. 7(B) is a cross-sectional view of an assembly of essential components. The I.I. comprises shutter 30, in the front, and window 31, multi-channel plate 32, scintillator 33 and optical fiber 34 arranged in the next stages of the shutter and having a light notification function. By arrangng such I.I. in front of the photo detector array 10 as necessary, it is possible to amplify very weak light and to detect photo emission more precisely.

The shutter of the I.I. is opened and closed in synchronism with the pulses of a laser and functions as a means for identifying the wavelength (l) of the atomic emission region and measuring the intensities of the plasma emission and atomic emission regions in a discriminating manner.

The laser beam is applied to the restriction portion of the cell with a power which is above the breakdown threshold of the emission from the particles and below the breakdown threshold of a medium, e.g. helium. The particles, when placed in a high density light, emit white light by being heated in picoseconds (ps) to nanoseconds (ns). Then, the particles are decomposed to an atomic level, positioned at an excited state, and emit fluorescence in approximately 10 ns. This emission is called "laser breakdown". For the photo emission due to breakdown, the emission occurs in the manner shown in FIG. 8.

Figure 8:
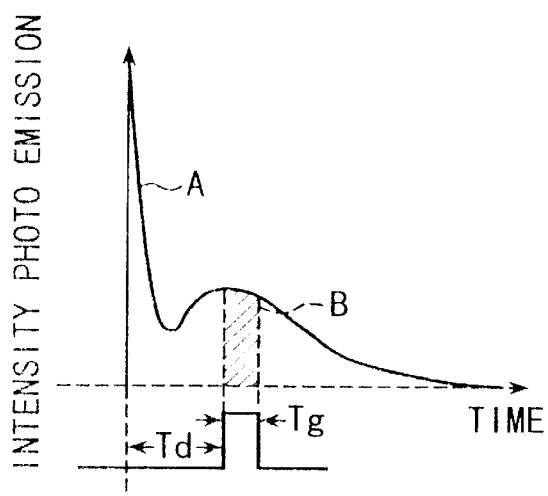
FIG. 8 is a graph depicting the status of the photo emission due to breakdown.

In FIG. 8, the portion shown by curve A indicates white light due to plasma emission and the portion shown by curve B indicates emission based on the type of element. Td shows the delay time and Tg shows the time of 0.1 to 0.5 $\mu$s during which the emission appears of an element specific wavelength and attenuates as time lapses. Such emissions are gathered with the optical fibers shown in FIG. 3, divided into spectral lines with grating 9 and are made incident to photo detector array 10. In addition, a signal processor is connected at the next stage of the photo detector array to process electrical signals from each element in the array, but is omitted in FIG. 3. The signal processor computes the size of the elements from the signal due to the intensity of white light and identifies components from the electrical signal of wavelength (1) generated after the delay of fixed time Td.

Figure 9:
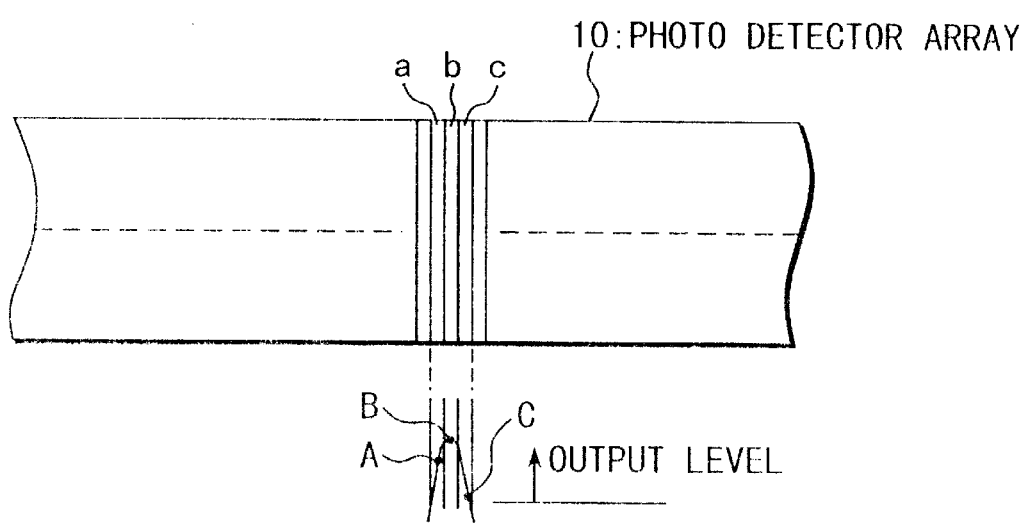
FIG. 9 is a view depicting a photo detector array used in the invention.

In the photo detector array used in the invention, at least three photo detectors are arranged for the wavelength emitted by an element shown in FIG. 9 and a peak of emission is determined from the output signals of the three photo detectors to identify an elemental component. In FIG. 9, it is assumed that the objects shown as portions a, b, and c are, for example, a photo diode array comprising the photo detector array and the output levels of the diodes are A,B, and C. Then, the emission peak of the element is determined as B and from this wavelength, the elemental component is identified. In addition, by providing a wavelength conversion element, such as scintillator, which may be coated with a phosphor, on the surface of the photo detector, emitted wavelengths can be shifted to the side having better sensitivity as a whole. Thus, wavelengths shorter than 0.2 $\mu$m for which a photo detector using silicon can only have a lower sensitivity, become easier to detect.

Each element has different emission intensities even when the particle size is the same. Thus, when equivalent particle sizes are to be measured, each element (for example 50 different kinds of elements) having known particle size should be made to produce emission by means of laser breakdown to determine in advance the relationship between the element size and the output signal. Furthermore, when an equivalent particle size is to be measured, the equivalent particle size should be estimated based on an average value obtained by the measurement of more than one particle. In this embodiment, although the description is of a medium carrying particles being helium gas, the medium is not limited to such gas. For example, a liquid, such as water, may be used.

Figure 1:
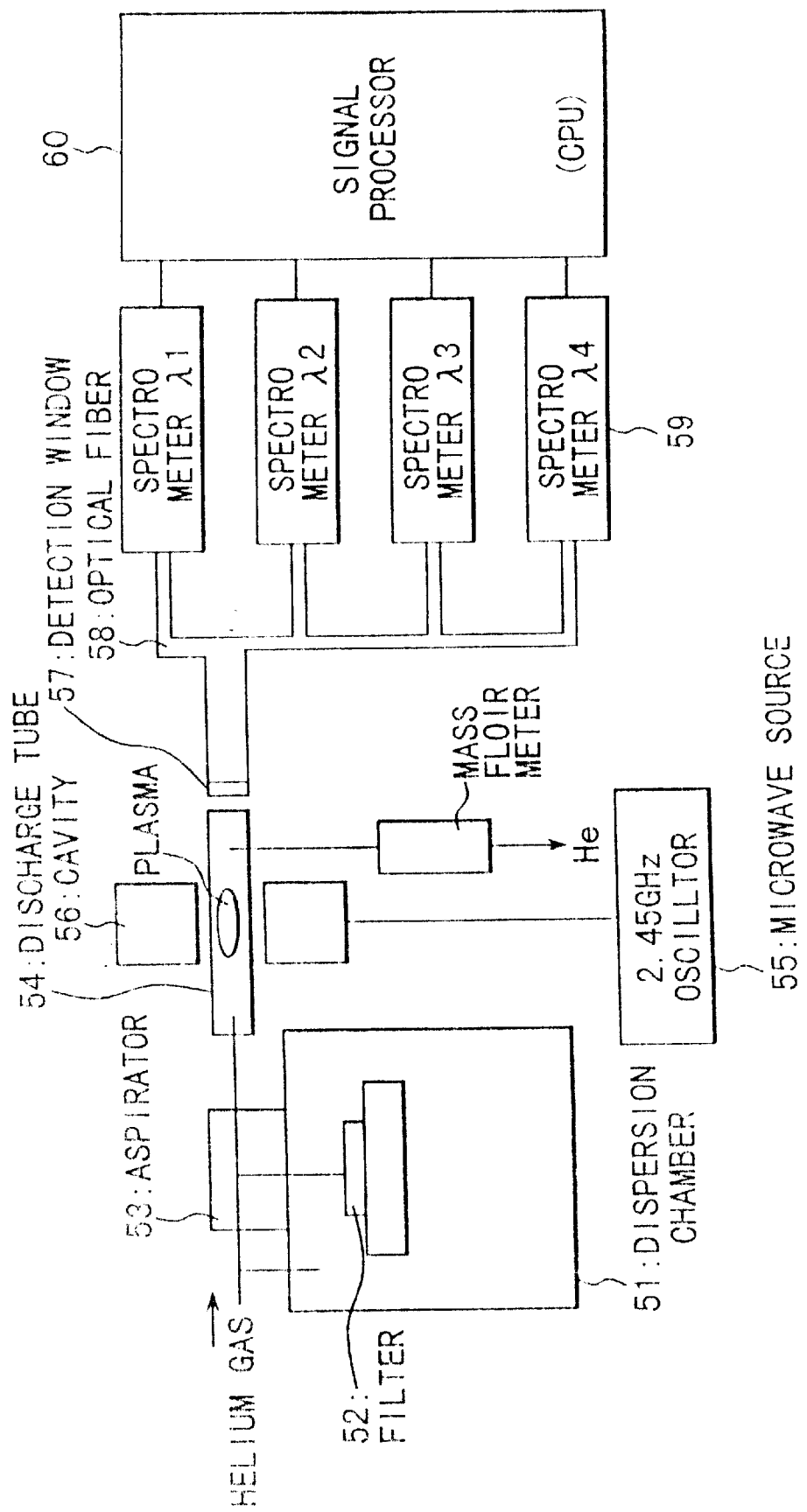
FIG. 1 is a diagram depicting a conventional particle analyzer system.

In addition, microwave plasma may also be used to cause photo emission of particles. In this case, microwave source 55, discharge tube 54, and cavity 56, of FIG. 1, are substituted for the vacuum cavity 1 shown in FIG. 3.

While the relationship shown in FIG. 2 between the atoms and the emission wavelengths includes both the part where emission wavelength of atoms are located thickly at the region A, and the part where the emission wavelengths of atoms are located thinly at the region B, in such a case, it is not advantageous in terms of costs that the entire photo detector array be subdivided to match the thick parts.

Thus, in the invention, more than one set of grating 9, photo detector array 10, etc, in spectrum detector is provided and the photo emission introduced into the parts is divided into more than one using optical fibers. The spectrum detector comprises the region shown as A and B and are measured separately. In that manner, at least the photo detector array to measure region B can be manufactured having a thin array.

The foregoing description is illustrative of the principles of the invention. Numerous extensions and modifications thereof would be apparent to the worker skilled in the art. All such extensions and modifications are to be considered to be within the spirit and scope of the invention.

What is claimed is:

1. A particle analyzer comprising:
   a cavity provided with a cell;
   a spectrum detector;
   means for introducing particles to be analyzed into said cell;
   means for applying a laser beam into said cavity to cause irradiation with said laser beam said particles within said cell to cause photo emission of said particles;
   fiber optic transmission means for gathering said photo emission over a wide range, and for concentrating and transmitting concurrently all of the gathered photo emission, said transmission means having one end thereof connected to said cavity and another end thereof connected to said spectrum detector and being a single line;
   blocking means connected directly to said one end of said transmission means and within said cavity for blocking from transmission by said transmission means wavelengths outside of said wavelengths of photo emission caused by said particles;
   grating means disposed within said spectrum detector for receiving all of the photo emission transmitted by said transmission means and for providing therefrom spectral lines thereof; and
   an array of a plurality of photo detectors parallely disposed within said spectrum detector, including at least three adjacent photo detectors, for detecting concurrently at least three adjacent ones of all of the spectral lines provided by said grating means thereby to identify a peak emission from the at least three adjacent photo detectors and thereby determine elemental components and sizes of said particles.

2. The system of claim 1, further comprising means for applying an alternating electric field to said particles introduced into said cells in advance.

3. A particle analyzer system comprising:
   a cavity provided with a cell;
   a spectrum detector;
   means for introducing particles to be analyzed into said cell;
   means for applying microwaves into said cavity to cause irradiation with microwave plasma said particles within said cell to cause photo emission of the particles;
   a single line fiber optic transmission means for gathering said photo emission over a wide range, and for concentrating and transmitting concurrently all of the gathered photo emission, said transmission means having one end thereof connected to said cavity and another end thereof connected to said spectrum detector;
   blocking means connected directly to said one end of said transmission means and within said cavity for blocking from transmission by said transmission means wavelengths not produced as photo emission by said particles;
   grating means disposed within said spectrum detector for receiving all of the photo emission transmitted by said transmission means and for providing therefrom spectral lines thereof; and
   an array of a plurality of photo detectors parallely disposed within said spectrum detector, including at least three adjacent photo detectors, for detecting concurrently at least three adjacent on of all of the spectral lines provided by said grating means thereby to identify a peak emission from the at least three adjacent photo detectors and thereby determine elemental components and sizes of said particles.

4. The system of claim 1 or 2, wherein said laser beam is a pulsed beam.

5. The system of claim 1 or 2, wherein output density of said light beam is set to a value higher than emission thesholds of said particles and lower than emission threshold of a medium.

6. The system of claim 1 or 3, wherein elemental components of particles are identified from atomic emission spectrum of said particles and equivalent particle size is measured by determining total of a plurality of atomic emission intensities.

7. The system of claim 1 or 2, wherein equivalent particle size is measured using plasma emission generated in an early time and elemental components of said particles are measured in a region where atomic emission can be seen after plasma emission is attenuated.

8. The system of claim 1 or 2, wherein are provided a shutter and a multi-channel plate comprising photo amplification means at a preceding stage of said photo detectors; whereby plasma emission is identified with atomic emission and very weak photo emission is amplified and said emission is guided to said photo detector means.

9. The system of claim 1, 2 or 3, wherein a wavelength conversion element is installed in front of photo diodes of said photo detector means, which have a region of wavelength shorter than 0.2 $\mu$m to detect atomic emission.

10. The system of claim 1, wherein equivalent particle size is measured by integrating emission intensity with respect to wavelength at an early time and elemental components are identified by photo emission of predetermined wavelength at a succeeding stage.

11. The system of claim 1 or 3, wherein an optical fiber is used to transmit photo emission down to vacuum ultraviolet wavelengths.

12. The system of claim 1, 2, or 3, wherein number of particles introduced into said cell is controlled by a particle concentration controller means.

13. The system of claim 1, 2, or 3, wherein said photo detector means is divided to enable peak values of each particle to be estimated.

14. The system of claim 1, 2, or 3, wherein refrigeration means is provided to cool said photo detector means.

15. The system of claim 1, 2 or 3, wherein photo emission is guided to a spectrometer and is divided into a plurality of channels using said photo emission transmission means and is detected with a plurality of spectrometers and photo detector means.

* * * * *